(12) United States Patent
Petit et al.

(10) Patent No.: US 10,576,110 B2
(45) Date of Patent: *Mar. 3, 2020

(54) ***LACTOBACILLUS JOHNSONII* LA1 NCC533 (CNCM I-1225) AND IMMUNE DISORDERS**

(75) Inventors: Valerie Petit, Palezieux (CH); Clara Garcia-Rodenas, Forel (CH); Monique Julita, Prilly (CH); Guenolee Prioult, Lausanne (CH); Annick Mercenier, Bussigny (CH); Sophie Nutten, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 393 days.

This patent is subject to a terminal disclaimer.

(21) Appl. No.: 13/319,632

(22) PCT Filed: May 7, 2010

(86) PCT No.: PCT/EP2010/056295
§ 371 (c)(1),
(2), (4) Date: Oct. 2, 2012

(87) PCT Pub. No.: WO2010/130662
PCT Pub. Date: Nov. 18, 2010

(65) Prior Publication Data
US 2013/0028877 A1    Jan. 31, 2013

(30) Foreign Application Priority Data

May 11, 2009   (EP) .................................... 09159925
May 11, 2009   (EP) .................................... 09159929

(51) Int. Cl.
*A61K 35/74*   (2015.01)
*A61K 35/745*  (2015.01)
(Continued)

(52) U.S. Cl.
CPC ............ *A61K 35/745* (2013.01); *A23K 10/18* (2016.05); *A23L 33/135* (2016.08); *A23L 33/40* (2016.08);
(Continued)

(58) Field of Classification Search
CPC .. A61K 35/747; A61K 35/744; A61K 35/741; A23V 2002/00; A23V 2200/324; A23L 1/3014; A23L 1/296
See application file for complete search history.

(56) References Cited

U.S. PATENT DOCUMENTS 5,578,302 A      11/1996  Brassart et al.
7,547,527 B2 *    6/2009  Baur et al. ...................... 435/41
(Continued)

FOREIGN PATENT DOCUMENTS

EP    1260227 A1 * 11/2002
EP    1593382        9/2005
(Continued)

OTHER PUBLICATIONS

Sgouras et al., Clinical and Diagnostic Laboratory Immunology, 12:1378-1386, 2005.*
(Continued)

*Primary Examiner* — Allison M Fox
*Assistant Examiner* — Qing Xu
(74) *Attorney, Agent, or Firm* — K&L Gates LLP

(57) ABSTRACT

The present invention generally relates to the field of preventing and/or treating inflammatory and infectious disorders, in particular by boosting the endogenous antimicrobial defences. One embodiment of the present invention is the use of non-replicating *L. johnsonii* La1 NCC533 (deposit number CNCM I-1225) for use in the treatment or prevention of disorders related to the immune system including infections.

12 Claims, 1 Drawing Sheet

Figure 1:
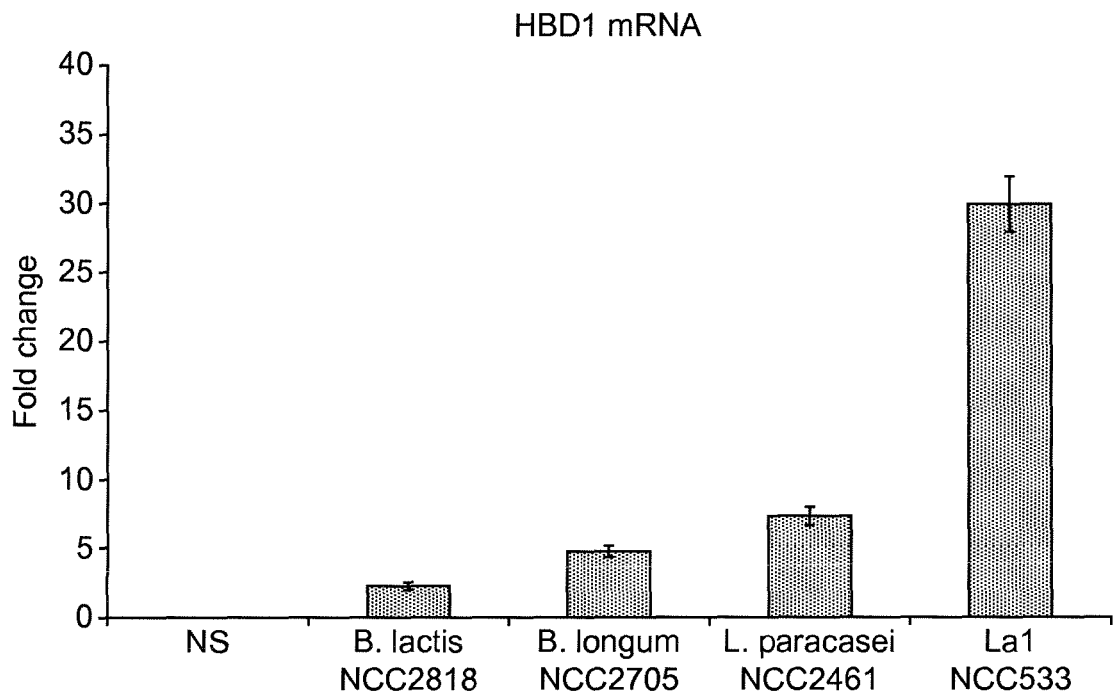

(51) Int. Cl.
*A61K 35/747* (2015.01)
*A23L 33/00* (2016.01)
*A23L 33/135* (2016.01)
*A23K 10/18* (2016.01)
*A61K 35/744* (2015.01)
*C12N 1/20* (2006.01)
*C12N 1/00* (2006.01)
*C12N 1/36* (2006.01)

(52) U.S. Cl.
CPC ............ *A61K 35/74* (2013.01); *A61K 35/744* (2013.01); *A61K 35/747* (2013.01); *C12N 1/005* (2013.01); *C12N 1/20* (2013.01); *C12N 1/36* (2013.01); *A23V 2002/00* (2013.01); *A23Y 2220/03* (2013.01); *A23Y 2220/15* (2013.01); *A23Y 2220/17* (2013.01); *A23Y 2220/43* (2013.01); *A23Y 2220/63* (2013.01); *A23Y 2220/71* (2013.01); *A23Y 2220/73* (2013.01); *A23Y 2240/41* (2013.01); *A23Y 2240/75* (2013.01); *A23Y 2300/29* (2013.01); *A23Y 2300/49* (2013.01); *A23Y 2300/55* (2013.01); *Y02A 50/473* (2018.01)

(56) References Cited

U.S. PATENT DOCUMENTS

| | | | |
|---|---|---|---|
| 2003/0049231 A1 | 3/2003 | Baur et al. | |
| 2003/0049240 A1* | 3/2003 | Ballevre | A23K 1/009 424/93.45 |
| 2004/0147010 A1 | 7/2004 | Vidal et al. | |
| 2005/0196480 A1 | 9/2005 | Sullivan et al. | |
| 2006/0002910 A1* | 1/2006 | Baur et al. | 424/93.45 |
| 2006/0008453 A1* | 1/2006 | Breton | A61K 8/19 424/93.45 |
| 2009/0035288 A1* | 2/2009 | Albers | A23C 9/12 424/93.45 |
| 2010/0254956 A1* | 10/2010 | Arulampalam | A23C 9/1234 424/93.45 |

FOREIGN PATENT DOCUMENTS

| | | |
|---|---|---|
| WO | WO0130365 | 5/2001 |
| WO | WO0152667 | 7/2001 |
| WO | 2007020884 | 2/2007 |
| WO | 2008141989 | 11/2008 |

OTHER PUBLICATIONS

Prantera et al., Gut, 51:405-409, 2002.*
Bajaj-Elliott et al., Gut, 51:356-361, 2002.*
Cole et al., Letters in Applied Microbiology, 11:233-235, 1990.*
Gardiner et al., Applied and Environmental Microbiology, 66(6):2605-2612, 2000.*
Cruchet et al., Nutrition, 19(9):716-721, 2003.*
Wikipedia—Coeliac disease, downloaded on Feb. 29, 2016 from https://en.wikipedia.org/wiki/Coeliac_disease.*
Wikipedia—Atopic dermatitis, downloaded on Feb. 29, 2016 from https://en.wikipedia.org/wiki/Atopic_dermatitis.*
What-is-Crohns-disease, downloaded on Feb. 29, 2016 from http://www.ccfa.org/what-are-crohns-and-colitis/what-is-crohns-disease/.*
Fang et al., European Journal of Clinical Investigation, 2003, 33: 82-87 (Year: 2003).*
Wang et al. "Bifodibacterium cell wall proteins induced beta-defensin 2 mRNA expression in human intestinal epithelial cells," Sichuan Daxue Xuebao, vol. 34, No. 4, pp. 622-624, XP003002759.

* cited by examiner

LACTOBACILLUS JOHNSONII LA1 NCC533 (CNCM I-1225) AND IMMUNE DISORDERS

CROSS REFERENCE TO RELATED APPLICATIONS

The present application is a National Stage of International Application No. PCT/EP2010/056295, filed on May 7, 2010, which claims priority to European Patent Application No. 09159925.8, filed on May 11, 2009 and European Patent Application No. 09159929.0, filed on May 11, 2009, the entire contents of which are being incorporated herein by reference.

The present invention generally relates to the field of preventing and/or treating inflammatory and infectious disorders, in particular by boosting the endogenous antimicrobial defences. One embodiment of the present invention is the use of non-replicating *L. johnsonii* La1 NCC533 (deposit number CNCM I-1225) for use in the treatment or prevention of disorders related to the immune system including infections.

Our environment is contaminated by a vast array of potentially pathogenic microorganisms. Skin keratinocytes, epithelial cells lining the gastrointestinal tract, respiratory tract, genitourinary tract all provide a physical barrier that protect against microbial intrusion into the body.

In addition, these epithelia contribute to the host defences by producing and secreting antimicrobials to limit access of bacteria and other microorganisms. These antimicrobial molecules constitute key components of the basic defence line of the innate immunity.

Defensins are one of the most important classes of antimicrobial peptides in humans. Defensins are produced by epithelial cells of the lung, skin, oral cavity, genitourinary, respiratory and gastrointestinal tract. Among these, there is the family of β-defensins including the defensin 1 (hBD1) and (hBD2).

HBD1 is expressed in various mucosal surfaces such as oral mucosa, salivary gland, stomach, small intestine, colon, liver and pancreas. HBD2 is also present in epithelial cells at multiple mucosal surfaces including that of gastrointestinal tract. Moreover, these two defensins are also present in saliva and airway surface fluid (Cunliffe, R. N. and Mahida, Y. R. 2004, J Leukoc. Biol. 75:49-58).

HBD1 is constitutively expressed and has never been shown to be consistently up-regulated by bacteria or inflammation (Ou, G., et al., 2009, Scand. J Immunol 69:150-161).

Probiotics are well known to be able to reinforce the various lines of gut defences: immune exclusion, immune elimination, and immune regulation. Probiotics are also known stimulate non-specific host resistance to microbial pathogens and thereby aid in their eradication.

However, despite this, the expression of the constitutive hBD1 has been reported as unaffected by probiotic bacteria (O'Neil, D. A. et al., *J Immunol* 163:6718-6724) and as very mildly upregulated by commensal (*Escherichia coli*) and pathogenic (*Salmonella typhimurium*) strains (Ou, G., et al., 2009, Scand. J Immunol 69:150-161).

The application of probiotics currently lies in reducing the risk of diseases associated with gut barrier dysfunction (E. Isolauri, et al, 2002, Gut 2002; 50:iii 54-iii 59). Probiotics are thought to be effective through survival in the gut, acid and bile stability, and temporal colonisation of the mucosal surfaces in the intestinal tract.

Therefore, the vast majority of published literature deals with live probiotics. However, several studies investigated the health benefits delivered by non-replicating bacteria and most of them indicated that inactivation of probiotics, e.g. by heat treatment, leads to a loss of their purported health benefit (Rachmilewitz, D., et al., 2004, Gastroenterology 126:520-528; Castagliuolo, et al., 2005, FEMS Immunol. Med. Microbiol. 43:197-204; Gill, H. S, and K. J. Rutherfurd, 2001, Br. J. Nutr. 86:285-289; Kaila, M., et al., 1995, Arch. Dis. Child 72:51-53.).

Working with viable bacteria in food products today has several disadvantages. Viable bacteria are usually not very stress resistant and are consequently difficult to handle in industrial scales while maintaining viability. Furthermore, for some product categories it may not be optimal to add viable micro-organisms to the formulation due to safety concerns. Hence, there is a need for bioactive non-viable micro-organisms.

Advantageously, the provision of non-replicating probiotic micro-organisms would allow the hot reconstitution, e.g., of powdered nutritional compositions while retaining health benefit for the consumer patient. Based thereon it may be desirable to work with non-replicating bacteria instead of their live counterparts, but the studies available in this respect are not encouraging.

The use of live probiotics as a strategy to treat or prevent inflammatory bowel diseases has been reported in the literature and recently reviewed by Dotan et al. (Dotan, I. and D. Rachmilewitz. 2005; Curr. Opin. Gastroenterol. 21:426-430). For, example, a highly concentrated cocktail of eight live probiotic bacteria (VSL #3) has been shown to be effective in prevention (Gionchetti, P., et al., 2003, Gastroenterology 124:1202-1209) and treatment of recurrent or refractory pouchitis in humans (Gionchetti, P., et al., 2000, Gastroenterology 119:305-309; Mimura, T., et al., 2004, Gut 53:108-114). Interestingly using a murine model of DSS-induced colitis, Rachmilewitz et al. (Rachmilewitz, D., et al., 2004, Gastroenterology 126:520-528) reported that treatments with viable and γ-irradiated VSL #3 but not heat-killed VSL #3 protect against colitis. Similarly heat-killed *L. crispatus* failed to protect against DSS-induced colitis while its viable counterpart clearly reduced the loss of body weight and the MPO activity in the gut (Castagliuolo, et al., 2005, FEMS Immunol. Med. Microbiol. 43:197-204). These studies suggest that probiotics are more effective alive in the context of gut inflammation than their non-replicating counterparts.

Inactivated *L. reuteri* (heat-killed and γ-irradiated) was found not to be able to decrease the TNFα-induced IL-8 production by T84 cells while its live counterpart exhibited a significant beneficial effect (Ma, D., et al., 2004, Infect. Immun. 72:5308-5314).

Hence, there is a need in the art for natural compositions that are easy to handle under industrial conditions, that are safe and easy to administer and that allow preventing and/or treating inflammatory and infectious disorders, in particular by boosting the endogenous antimicrobial defences.

Ideally the natural composition should be prepared from probiotic cultures, in particular from a probiotic micro-organism that is well accepted today and recognized by consumers for delivering heath benefits. Advantageously, the composition should contain non-replicating bacteria and should be more effective than their live counterpart.

The present inventors have addressed this need.

Hence, it was the object of the present invention to improve the state of the art and to provide a natural composition, that allows preventing and/or treating inflammatory and infectious disorders, in particular by boosting the endogenous antimicrobial defences and that fulfils the requirements listed above.

The inventors were surprised to see that they could achieve the object of the present invention by the subject matter of the independent claims. The dependant claims further define preferred embodiments of the present invention.

The subject matter of the present invention strengthens the mammalian endogenous antimicrobial defences by administering a product containing micro-organisms, such as non-replicating micro-organism, for example heat-treated microorganisms.

The inventors describe that *L. johnsonii* (La1, NCC 533, deposit number CNCM I-1225), in particular non-replicating *L. johnsonii* (La1, NCC 533, deposit number CNCM I-1225), for example heat treated *L. johnsonii* (La1, NCC 533, deposit number CNCM I-1225), has superior effects on the induction of antimicrobial peptide expression than those previously identified and described in the literature.

It was found, for example, that:

*L. johnsonii* (La1, NCC 533, deposit number CNCM I-1225) strongly induces the constitutive hBD1 expression, and that Heat-treated *L. johnsonii* (La1, NCC 533, deposit number CNCM I-1225) up-regulates hBD1 more strongly than its live counterpart.

HBD1 displays antibacterial activity against a broad spectrum of bacteria including *E. coli* and *Pseudomonas aeruginosa, H. pylori* (Nuding, S., et al., 2009, Microbes. Infect. 11:384-393) and also against yeasts such as *Candida albicans* (O'Neil, D. A. 2003, Mol. Immunol 40:445-450) and viruses (human immunodeficiency virus) (Kota, S. Et al., 2008, J. Biol. Chem 283:22417-22429). Thus, these antimicrobial peptides may reinforce the mucosal barrier and consequently limit bacterial adherence and invasion.

More and more evidence indicate that the levels of defensins are reduced in certain pathophysiological conditions and that this is a risk factor in the pathogenesis and complications of infectious and inflammatory diseases such as (Doss, M. et al., 2010, J Leukoc. Biol. 87:79-92); Rivas-Santiago, B. et al., 2009, Infect. Immun. 77:4690-4695):

In the respiratory tract:
cystic fibrosis, reactive airways disease, lung infections and tobacco smoking, asthma, pneumonia, rhinitis, otitis, sinusitis, tuberculosis In the gastrointestinal tract:
Crohn's disease (colon and ileum), ulcerative colitis, gastritis and gastric ulcer induced by *Helicobacter pylori* infection, infectious diarrhea, necrotising enterocolitis, antibiotic-associated diarrhea, celiac disease, intestinal immaturity.

In the genitourinary tract:
Bacterial vaginosis, HIV, Herpes simplex virus, urinary infection In the skin:
Atopic dermatitis, chronic ulcer, carcinoma, atopic eczema, burn injury In the oral cavity:
HIV patients, tonsillitis, gingivitis, dental caries
Keratitis in eyes The results presented herein indicate that *L. johnsonii* La1 (NCC 533, deposit number CNCM I-1225) has a stronger capacity to boost the endogenous antimicrobial defence than previously identified probiotic bacteria, and thus may be more efficient in the prevention and treatment of SIBO (small intestinal bacterial overgrowth), inflammatory and infectious disorders.

In addition, the inventors data indicate—contrary to what would be expected from the literature—that heat treatment does not decrease, but further increases the strong antimicrobial effect of *L. johnsonii* La1 (NCC533, deposit number CNCM I-1225).

One embodiment of the present invention is a composition comprising *L. johnsonii* La1 (NCC533, deposit number CNCM I-1225) for use in the treatment or prevention of disorders linked to the immune system, including infections.

According to the present invention the disorders linked to the immune system may be treated or prevented by increasing endogenous hBD1 expression.

The present invention also relates to a composition comprising *L. johnsonii* La1 (NCC533, deposit number CNCM I-1225) for use in the treatment or prevention of disorders linked to a decreased hBD1 expression, such as microbial infections, for example.

The present invention also concerns the use of *L. johnsonii* La1 (NCC533, deposit number CNCM I-1225) in the preparation of a composition for the treatment or prevention of disorders linked to the immune system.

Non-replicating *L. johnsonii* La1 (NCC533, deposit number CNCM I-1225) may be used at least partially. Non-replicating, in particular heat treated, *L. johnsonii* La1 (NCC533, deposit number CNCM I-1225) have the advantage of being even more effective than their live counterpart.

The use of non-replicating microorganisms, such as heat-treated *L. johnsonii* La1 (NCC533, deposit number CNCM I-1225), instead of their live counterparts, has further the advantages to:

reduce the potential risk of live probiotic-associated sepsis in the sensitive targeted populations, represent a safe alternative to immunocompromised patients, and lower processing hurdles, can be integrated in shelf stable liquid products with an long shelf life.

Hence, in one embodiment of the present invention at least 90%, for example at least 95% preferably at least 98%, most preferably at least 99%, ideally at least 99.9%, or all of the *L. johnsonii* La1 (NCC533, deposit number CNCM I-1225) are non-replicating.

The present invention also relates to a composition comprising *L. johnsonii* La1 (NCC533, deposit number CNCM I-1225), wherein at least 95% preferably at least 98%, most preferably at least 99%, ideally at least 99.9%, or 100% of the *L. johnsonii* La1 (NCC533, deposit number CNCM I-1225) are non-replicating.

Thus, the present invention also relates to bioactive, non-replicating, e.g., heat treated, *L. johnsonii* La1 (NCC533, deposit number CNCM I-1225).

"Non-replicating" *L. johnsonii* La1 (NCC533, deposit number CNCM I-1225) include *L. johnsonii* La1, which have been heat treated. This includes *L. johnsonii* La1 (NCC533, deposit number CNCM I-1225) that are inactivated, dead, non-viable and/or present as fragments such as DNA, metabolites, cytoplasmic compounds, and/or cell wall materials.

"Non-replicating" means that no viable cells and/or colony forming units can be detected by classical plating methods. Such classical plating methods are summarized in the microbiology book: James Monroe Jay, Martin J. Loessner, David A. Golden. 2005. Modern food microbiology. 7th edition, Springer Science, New York, N.Y. 790 p. Typically, the absence of viable cells can be shown as follows: no visible colony on agar plates or no increasing turbidity in liquid growth medium after inoculation with different concentrations of bacterial preparations ('non replicating' samples) and incubation under appropriate conditions (aerobic and/or anaerobic atmosphere for at least 24 h).

The *L. johnsonii* La1 (NCC533, deposit number CNCM I-1225) may be rendered non-replicating by heat inactivation. Heat inactivation may occur at at least about 70° C.

Any heat treatment may be used to inactivate the probiotics as long as it is carried out long enough to achieve inactivation. For example, such a heat treatment may be carried out for at least 10 seconds.

Typically a high temperature will require a short heating time, while lower temperatures will require longer heating.

For example, the *L. johnsonii* La1 (NCC533, deposit number CNCM I-1225) may be rendered non-replicating at 110° to 140° for 1-30 seconds, e.g. 10-20 seconds.

This given time frame refers to the time the *L. johnsonii* La1, are subjected to the given temperature. Note that depending on the nature and amount of the composition the *L. johnsonii* La1 are provided in and depending on the architecture of the heating apparatus used, the time of heat application may differ. The temperature treatment may be carried out at normal atmospheric pressure but may be also carried out under high pressure. Typical pressure ranges are form 1 to 50 bar, preferably from 1-10 bar, even more preferred from 2 to 5 bar. An ideal pressure to be applied will depend on the nature of the composition which the microorganisms are provided in and on the temperature used.

If the compositions the La1 (NCC533, deposit number CNCM I-1225) are provided in are anyway heat treated, e.g., before they are packaged and distributed, it may be preferable to use this heat treatment step to inactivate La1 NCC533.

Typically, compositions containing La1 (NCC 533, deposit number CNCM I-1225) may be treated by a high temperature short time (HTST) treatment, flash pasteurization or an ultra high temperature (UHT) treatment.

A UHT treatment is Ultra-high temperature processing or a ultra-heat treatment (both abbreviated UHT) involving the at least partial sterilization of a composition by heating it for a short time, around 1-10 seconds, at a temperature exceeding 135° C. (275° F.), which is the temperature required to kill bacterial spores in milk. For example, processing milk in this way using temperatures exceeding 135° C. permits a decrease of bacterial load in the necessary holding time (to 2-5 s) enabling a continuous flow operation.

There are two main types of UHT systems: the direct and indirect systems. In the direct system, products are treated by steam injection or steam infusion, whereas in the indirect system, products are heat treated using plate heat exchanger, tubular heat exchanger or scraped surface heat exchanger. Combinations of UHT systems may be applied at any step or at multiple steps in the process of product preparation.

A HTST treatment is defined as follows (High Temperature/Short Time): Pasteurization method designed to achieve a 5-log reduction, killing 99.9999% of the number of viable micro-organisms in milk. This is considered adequate for destroying almost all yeasts, molds and common spoilage bacteria and also to ensure adequate destruction of common pathogenic heat resistant organisms. In the HTST process milk is heated to 71.7° C. (161° F.) for 15-20 seconds.

Flash pasteurization is a method of heat pasteurization of perishable beverages like fruit and vegetable juices, beer and dairy products. It is done prior to filling into containers in order to kill spoilage micro-organisms, to make the products safer and extend their shelf life. The liquid moves in controlled continuous flow while subjected to temperatures of 71.5° C. (160° F.) to 74° C. (165° F.) for about 15 to 30 seconds.

For the purpose of the present invention the term "short time high temperature treatment" shall include high-temperature short time (HTST) treatments, UHT treatments, and flash pasteurization, for example.

The compositions of the present invention may comprise La1 in an amount sufficient to at least partially treat infections and disorders linked to the immune system and/or their complications. An amount adequate to accomplish this is defined as "a therapeutically effective dose". Amounts effective for this purpose will depend on a number of factors known to those of skill in the art such as the severity of the disease and the weight and general health state of the consumer, and on the effect of the food matrix.

In prophylactic applications, compositions according to the invention are administered to a consumer susceptible to or otherwise at risk of disorders linked to the immune system in an amount that is sufficient to at least partially reduce the risk of developing such disorders. Such an amount is defined to be "a prophylactic effective dose". Again, the precise amounts depend on a number of patient specific factors such as the patient's state of health and weight, and on the effect of the food matrix.

Those skilled in the art will be able to adjust the therapeutically effective dose and/or the prophylactic effective dose appropriately.

In general the composition of the present invention contains La1 (NCC533, deposit number CNCM I-1225) in a therapeutically effective dose and/or in a prophylactic effective dose.

Typically, the therapeutically effective dose and/or the prophylactic effective dose is in the range of about 0.005 mg-1000 mg La1 per daily dose.

In terms of numerical amounts, La1 (NCC533, deposit number CNCM I-1225) may be present in the composition in an amount corresponding to between $10^4$ and $10^{12}$ equivalent cfu/g of the dry composition. Obviously, non-replicating micro-organisms do not form colonies, consequently, this term is to be understood as the amount of non replicating micro-organisms that is obtained from $10^4$ and $10^{12}$ cfu/g replicating bacteria. This includes micro-organisms that are inactivated, non-viable or dead or present as fragments such as DNA or cell wall or cytoplasmic compounds. In other words, the quantity of micro-organisms which the composition contains is expressed in terms of the colony forming ability (cfu) of that quantity of micro-organisms as if all the micro-organisms were alive irrespective of whether they are, in fact, non replicating, such as inactivated or dead, fragmented or a mixture of any or all of these states.

For example, the composition in accordance with the present invention may contain an amount of *L. johnsonii* La1 (NCC533, deposit number CNCM I-1225) corresponding to about $10^4$ to $10^{12}$ cfu per daily dose.

The composition of the present invention may contain about 0.005 mg-1000 mg *L. johnsonii* La1 (NCC533, deposit number CNCM I-1225) per daily dose.

The composition of the present invention may be any kind of composition. The composition may be to be administered orally, enterally, parenterally (subcutaneously or intramuscularly), topically or ocularly, or by inhalation, intrarectally and intravaginally for example.

Hence, the composition of the present invention may be selected from the group consisting of food compositions, food products including pet foods, drinks, formulas for complete nutrition, nutritional supplements, nutraceuticals, food additives, pharmaceutical compositions, cosmetical compositions, medicaments, and topical compositions.

Prebiotics may be added. Prebiotics may support the growth of probiotics before they are rendered non-replicating. Prebiotics may also act synergistically with viable probiotic bacteria that are present in the composition and/or that may be added.

The disorder linked to the immune system may be selected from the group consisting of infections, in particular bacterial, viral, fungal and/or parasite infections; inflammations; phagocyte deficiencies; epithelial barrier defects, immune system immaturity, SIBO and combinations thereof.

In one embodiment of the present invention the composition comprising *L. johnsonii* La1 (NCC533, deposit number CNCM I-1225) may be for use in the treatment or prevention of microbial infections, such as viral, fungal and/or parasite infections.

The disorder linked to the immune system may also be selected from the group of disorders linked to a reduced level of defensins, in particular hBD1. Such disorders may be selected from the group consisting of cystic fibrosis, reactive airways disease, lung infections from tobacco smoking, asthma, pneumonia, rhinitis, otitis, sinusitis, tuberculosis, Crohn's disease (colon and ileum), ulcerative colitis, celiac disease, intestinal immaturity, gastritis and gastric ulcer induced by *Helicobacter pylori* infection, infectious diarrhea, necrotising enterocolitis, antibiotic-associated diarrhea, bacterial vaginosis, HIV, Herpes simplex virus, urinary infection, atopic dermatitis, chronic ulcer, carcinoma, atopic eczema, burn injury, tonsillitis, gingivitis, dental caries, keratitis in eyes, and combinations thereof.

The composition of the present invention may be used to boost the endogenous antimicrobial defences.

This may be achieved, for example, by boosting the endogenous hBD1 expression.

The present inventors have found that *L. johnsonii* La1 (NCC533, deposit number CNCM I-1225) strongly induces the constitutive hBD1 expression, and that non-replicating, e.g. heat treated, *L. johnsonii* La1 (NCC533, deposit number CNCM I-1225) up-regulates hBD1 expression even more than its live counterpart.

Consequently, the subject matter of the present invention also embraces a method to increase the effectiveness of *L. johnsonii* La1 (NCC533, deposit number CNCM I-1225) in the treatment or prevention of disorders linked to the immune system comprising the step of rendering *L. johnsonii* La1 (NCC533, deposit number CNCM I-1225) non-replicating, e.g., by heat treatment.

The disorder linked to the immune system may be one of the disorders listed above, for example.

In one embodiment of the present invention the method comprises a heat treatment step at at least about 70° C. for at least about 10 seconds.

Those skilled in the art will understand that they can freely combine all features of the present invention described herein, without departing from the scope of the invention as disclosed. In particular, features described for the compositions of the present invention may be applied to the uses and/or to the method of the present invention and vice versa.

Further advantages and features of the present invention are apparent from the following Examples and Figures.

FIG. 1 shows that heat treated La1 (NCC533, deposit number CNCM I-1225) at 120° C.-15 sec strongly induces hBD1 mRNA in intestinal epithelial cells in vitro compared with other heat-treated strains. T84 cells were incubated for 4 h with the heat-treated strains. Gene expression of hBD1 was analyzed by real-time PCR. The bars represent the means±sem normalized to basal expression of non stimulated cells.

Figure 2:
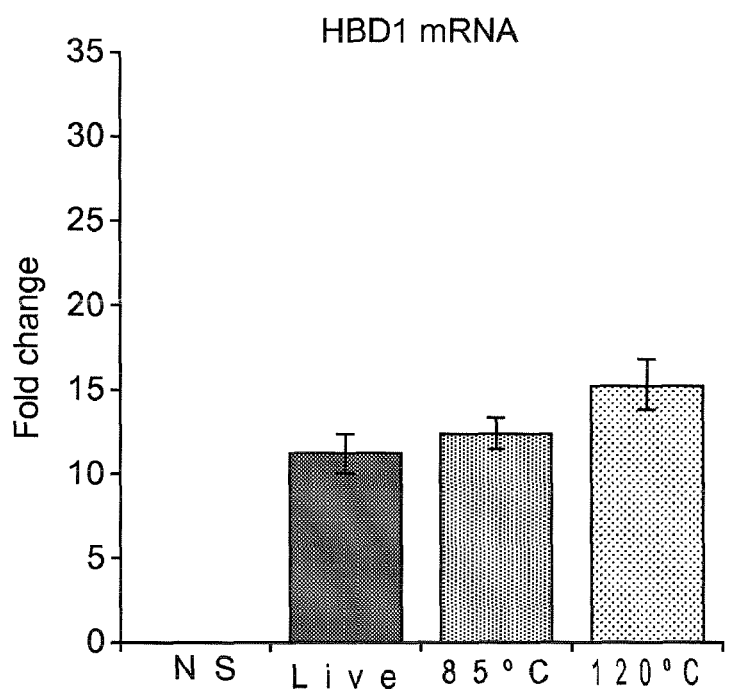

FIG. 2 shows that a high temperature and short time treatment of La1 (NCC533, deposit number CNCM I-1225) tends to be the best to induce hBD1 mRNA expression. T84 cells were stimulated for 4 h with the live and heat-treated La1 (NCC533, deposit number CNCM I-1225) at 120° C.—15 sec or 85° C.—20 min. Gene expression of hBD1 was analyzed by real-time PCR. The bars represent the means±sem normalized to basal expression of non stimulated cells.

EXAMPLES

Experimental Protocol:

T84 cells were used from passage 30-40 and cultured in Dulbecco's modified essential medium/F-12 (Sigma D 6421) containing 5% of foetal calf serum (FCS) (Amined BioConcept) and 2 mM glutamine. Cells were seeded at a concentration of $2\times10^6$ cell/well in 6-well culture plates and grown as monolayers at 37° C. in a 5% $CO_2$—95% air atmosphere. Cells grown to 1 week after confluence were incubated with serum and antibiotic-free medium for at least 12H. This step was necessary to eliminate serum-induced defensin expression and prevent any influence of antibiotics on the probiotics and on the cell immune response. Cells were further incubated with probiotics or heat-treated strains for 4H. At the end of the incubation time, cells were washed with PBS and harvested with TriPure™ isolation reagent according to the supplier's protocol. Human hBD1 and hBD2 gene expression in the so-treated cells was assessed by quantitative PCR.

Bacterial strains used in this experiment are *B. longum* (NCC 2705, deposit number CNCM I-2618), *B. lactis* (NCC 2818, deposit number CNCM I-3446), *L. johnsonii* (La1, NCC 533, deposit number CNCM I-1225), *L. paracasei* (ST11, NCC 2461, deposit number CNCM I-2116). These strains were tested live or heat-treated at either 120° C.—15 sec or 85° C.—20 min.

Results:

Heat-treated La1 (NCC533, deposit number CNCM I-1225) at 120° C., 15 sec induced strongly hBD1 mRNA expression after 4 h of incubation (FIG. 1) in contrast to the other tested heat-treated strains. These data are unique, as HBD1 expression, which is constitutively expressed, is currently thought by the scientific community as virtually non modulable by microbes, microbial products or inflammation.

Both live and heat-treated La1 (NCC533, deposit number CNCM I-1225) strongly induced hBD1 mRNA expression, but the highest induction of hBD1 was elicited by heat-treated La1 (high temperature and short time treatment) (FIG. 2).

The invention claimed is:

1. A method for treatment of a disorder selected from the group consisting of Crohn's disease, infectious diarrhea, antibiotic-associated diarrhea, gingivitis, and combinations thereof, the method comprising administering a composition comprising *Lactobacillus johnsonii* La1 (NCC533, deposit number CNCM I-1225) to an individual having the disorder, wherein the *L. johnsonii* La1 is rendered non-replicating by a heat treatment at a temperature of 110° C. to 140° C. for 1-30 seconds.

2. The method in accordance with claim 1, wherein the heat treatment is carried out for at least 10 seconds.

3. The method in accordance with claim 1, wherein the composition is administered to the individual in an amount that provides $10^4$ to $10^{12}$ cfu of the *L. johnsonii* La1 (NCC533, deposit number CNCM I-1225) per day.

4. The method in accordance with claim 1, wherein the composition is administered to the individual in an amount that provides about 0.005 mg 1000 mg of the *L. johnsonii* La1 (NCC533, deposit number CNCM 1-1225) per day.

5. The method in accordance with claim 1, wherein the composition is selected from the group consisting of food compositions, food products, drinks, formulas for complete nutrition, nutritional supplements, nutraceuticals, food additives, pharmaceutical compositions, cosmetical compositions, topical compositions, and medicaments.

6. The method in accordance with claim 1, wherein the composition increases endogenous hBD1 expression.

7. The method of claim 1, wherein the heat treatment is at 120° C. for 15 seconds.

8. The method of claim 1, wherein the composition increases endogenous antimicrobial defences.

9. A method to increase the effectiveness of *L. johnsonii* La1 (NCC533, deposit number CNCM I-1225) in treatment of a disorder selected from the group consisting of Crohn's disease, infectious diarrhea, antibiotic-associated diarrhea, gingivitis, and combinations thereof, the method comprising: rendering the *L. johnsonii* La1 non-replicating by a heat treatment at a temperature of 110° C. to 140° C. for 1-30 seconds; and administering the non-replicating *L. johnsonii* La1 to a patient having the disorder.

10. The method in accordance with claim 9, wherein the *L. johnsonii* La1 (NCC533, deposit number CNCM 1-1225) are rendered non-replicating by the heat treatment for at least 10 seconds.

11. The method of claim 9, wherein the heat treatment is at 120° C. for 15 seconds.

12. The method of claim 9, wherein the heat treatment is performed for 10 to 20 seconds.

\* \* \* \* \*